US009458505B2

United States Patent
Eng

(10) Patent No.: US 9,458,505 B2
(45) Date of Patent: Oct. 4, 2016

(54) DIAGNOSIS OF COWDEN AND COWDEN-LIKE SYNDROME BY DETECTION OF DECREASED KILLIN EXPRESSION

(71) Applicant: Charis Eng, Cleveland Heights, OH (US)

(72) Inventor: Charis Eng, Cleveland Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

(21) Appl. No.: 13/721,696

(22) Filed: Dec. 20, 2012

(65) Prior Publication Data

US 2013/0157958 A1    Jun. 20, 2013

Related U.S. Application Data

(60) Provisional application No. 61/578,061, filed on Dec. 20, 2011.

(51) Int. Cl.
 *C12Q 1/68* (2006.01)
 *C07H 21/04* (2006.01)

(52) U.S. Cl.
 CPC ........... *C12Q 1/6883* (2013.01); *C12Q 1/6886* (2013.01); *C12Q 2600/154* (2013.01); *C12Q 2600/158* (2013.01)

(58) Field of Classification Search
 None
 See application file for complete search history.

(56) References Cited

U.S. PATENT DOCUMENTS 7,576,191 B2 * 8/2009 Liang et al. ................. 536/23.1
2012/0264631 A1  10/2012 Eng et al.

OTHER PUBLICATIONS

Bennett et al (JAMA et al. vol. 304, No. 24, pp. 2724-2732, Dec. 24, 2010).*
Bennett et al (Genes, Chromosomes, & Cancer, vol. 50, pp. 654-661, May 16, 2011).*
Jelovac et al. (JAMA, vol. 304, No. 24, pp. 2744-245, Dec. 2010).*
Garcia et al. (Genes, Chromosomes & Cancer, vol. 41, pp. 117-124, 2004).*
Report on KILLIN Methylation and Risk of Multiple Cancers. SciTech Patent-Art, Hyderabad, India, Nov. 18, 2010, pp. 1-9.
Eng. Transcription Factor KLLN inhibits Tumor Growth by AR Suppression . . . , The Jrnl. of Clinical Endocrinology & Metabolism.
Bennett, et al. Germine Epigenetic Regulation of Killin in Cowden . . . JAMA, 12-22/29/2010, vol. 304, No. 24, pp. 2724-2738.

(Continued)

*Primary Examiner* — Jeanine A Goldberg
(74) *Attorney, Agent, or Firm* — Tarolli, Sundheim, Covell & Tummino LLP

(57) ABSTRACT

A method of diagnosing Cowden syndrome (CS) and Cowden-like Syndrome (CLS) is described. The method includes diagnosing CS and CLS in a subject by identifying a decrease in expression of the KILLIN gene, or by identifying hypermethylation of the KILLIN promoter region. Kits for diagnosing CS and CLS by identifying subjects having KILLIN promoter region hypermethylation and primers specific for a methylated KILLIN promoter region are also described.

9 Claims, 7 Drawing Sheets

(56) References Cited

OTHER PUBLICATIONS

Tada et al. Epigenetic Modulation of Tumor Suppressor . . . Jnl. of Nat'l Cancer Inst., vol. 98, No. 6, Mar. 15, 2006, pp. 396-406.
Bennett et al., Tumor Suppressor Activity of CCAAT/Enhancer Binding, www.aacrjournals.or, 2007, pp. 4656-4664, downloaded from cancerres.aacrjournals.org on Dec. 7, 2012.
Yu, et al. Androgen Receptor-Induced Tumor Supporessor, KLLN . . . , Human Molecular Genetics, pp. 1-38, Oct. 10, 2012.
Cho et al. Killin is a P53-Regulated Nuclear . . . , The Nat'l Academy of Sciences of the USA, pp. 5396-5401, vol. 105, No. 14, Apr. 8, 2008.
Bennett et al., Germline and Somatic DNA Methylation and Epigenetic Regulation . . . , Genes , Chromosones & Cancer 50:654-661, 2011.
Nizialek, et al. Germline and Somatic Klln Alterations in Breast Cancer . . . Jnl. of Human Molecular Genetics, pp. 1-33.

* cited by examiner

SEQ ID NO: 1 -                                              SEQ ID NO: 3 (within brackets lines 3-7)

[CATGTCTGGGAGCCTGTGGCTGAAGAAAAAGGAGGAGAGAGATGGCAGAAGCTGCTGGTGGCGGGGCTTCTTC
TGCAGGATGGAAATGGCTCTGGACTTGGCGGTAGCTGATGCCCCTCGCTCTGCCGCCGCTTGGCTCTGGACCGCA
GCCGGGTAATGGCTGCTGCGGCGGCTGCTGGATGGTTGCAGC[GACTGGGCCTGCTTCTCCTCAGCAGCCAGAGG
CCTGGCAGCGGCGGCAGCGGAATGGGGAGAAGACGAATAATCCTCCGAACGGCTGCCTCCGCCGGCGGCCTCCG
GAGCCCGGGCCACGGGGGGTGCGGCGGCGGCGCACGGGAGGTTTAAAACCGGCCCGGGTCCCTGGATGTGCCA
GCCGCCGCCGCCGTGTTGGAGGCAGTAGAAGGGGAGAGACCAACTCTCCGGCGTTCCCAGCCCTGGAAATG
GTGACAGGCGACTCAGACCCCCTCCCTGGAGCTGCAG]CCGCCGCGGCCGCCGCCGCCGCCGCTTCTCCCCCCCGC
TCCAGGAGCGGGAGGTGCCGCCGCCGCCGCCGCGCCTCAGCCGGCTCCCGCCCGAGCCCACGGCTTCCACCTTCC
CTTTCAGGAGAAGCCGAGGAAGAGGCTGCACGGTTAGAAAAGACGAAGAGGAGGCGAGAAACGCCGCCGCTGC
CGCCGCCGCAGGCCGGCCGGCTCCCCGAGGGCGCTGCCCCCGCGGCTGCTCACAGGCGCTGAGAGGGGCTCCGG
GCCGCGGCCGCCGCCGTCTCTCATCTCCCTCGCCTGAGCCCGGCCTCGCCTCACAGCGGCTCAACTCTCAAACTTCC
ATCATGGCTGCAGCTTCCGAGAGGAGAGAACTGAGCGCAGTCGCGTCCCAGCGCCGAGCGCGTATCCTGCCGCA
GCGCATAAAGAGTCCCGCCACATCACCGCCCGCCGGCCTGCCCGCCCCCTCCGCCGCCGCGCCGGGAGCCCGGGC
GCCTCGGAAGACCGAGGGGAGGCGGGAGGCGAGCGAGAGGCGGACGGGACCGCGCCGGGCGAGGGGAGG]

[GCAGGGCAGGGCAGGGGGCGGTAGGAGGGGGCAGAGCGGTAGCTCTGGGTGCGAGCGCAGAGTCCCCAAGC
CGCAGGCTCTACTGAGCATGCCCAGTGTAGCTGCCTGGGGCTTGCTCGGGCCGGTTCCCAGCCGCCAGCCTGCAG
CTGCACTTGCTGCGGCTTTTGCAGCAACGCGAGGCGAGGATAACGAGCTAAGCCTCGGCCTCTGCCCAGAAACCC
AGCCGGAGGCAGGGTAGGCTGTTGTGGGCGGGGGTGGAGGACTGATGATGAAAGCTGAGATGGGTGCGTTGA
GCAGTGTCACTGACTCGAGTCTGAGGTTACCTGTGCACAGGTGAAAAGGACCAGGTGACCACGCTGCTCAGTGTA
GAGGGAAATGCAGGGACGGTCCCTGCAAGGGGAATACCCTCCCCCCTTGCCTCTACCCCTAGATTTCCGCGGCGT
GGACTGCATTCGCTCTTTCCTTTTGCACCGCTGTCGGATCACAATCGTTCGCAGAGATTTGACTGTAACAGCCTTTG
CCTAGAGATTCCCCCTTCCCCCAAATCTGTGTCCTCATGGTGTCAGTCTTAGCACAAAGAGCAACCTGCTATTGTGT
CGCCAGCGTGTATCACCTCATCCGGCTCCCTTGCAGCGCCCCACCTCTCGCTTCCCCGGTAACTCGGCTCGTTTGCC
CTAAAAATGAAAGCTCTCAGCCGAGCGTGCTGAACGTGAACACATAGCCGTTGAATTTCAAGGGCCCAAAGGGCA
CCTATCTAAATGAACTGAAAGAGGATCCCTGTGAGTGGGACGCACCCCGCAGGCCTCTCCTGCGCCCGCTCCGGT
GCCCCCAAGAGAGTCGAGCATCTTTCCCCTCGGGCTCCAGGTCGGTTCGCGGCGTCGGAGTCAAGCTCGGTTCTCA
GAGACCACCTAGCCCCGCCCCCCCTTGGCCGCCGTGAAAACCCGGCAGGATG] – SEQ ID NO: 2

FIG. 1

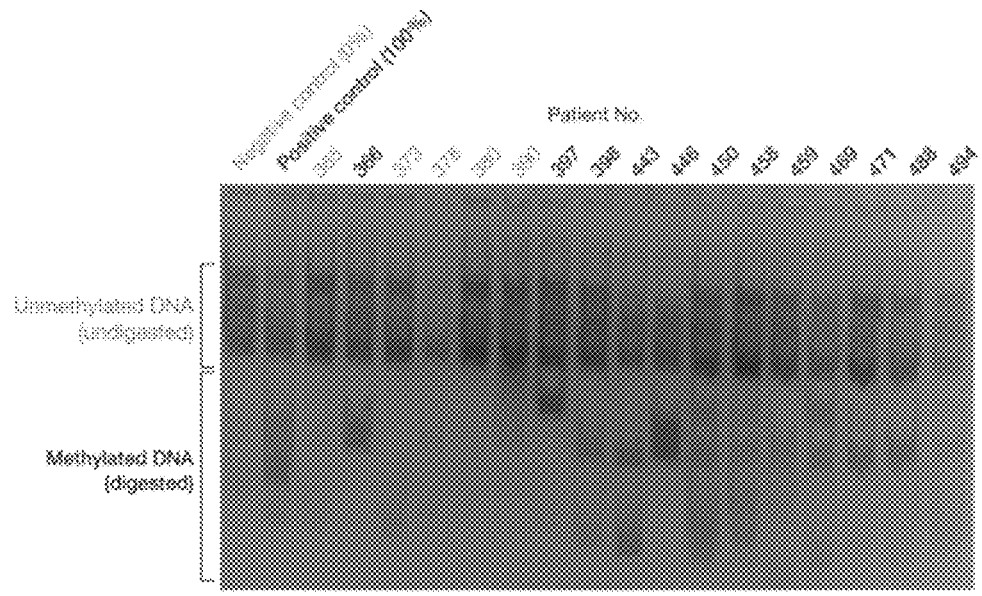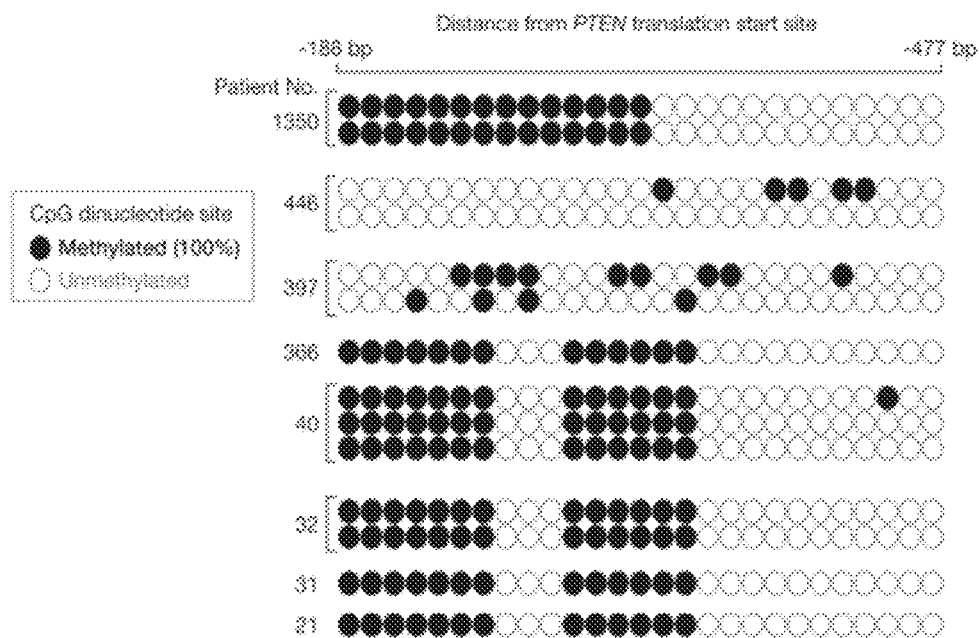
FIG. 3

SEQUENCE LISTING

```
<160> NUMBER OF SEQ ID NOS: 17

<210> SEQ ID NO 1
<211> LENGTH: 1035
<212> TYPE: DNA
<213> ORGANISM: Homo sapiens

<400> SEQUENCE: 1
catgtctggg agcctgtggc tgaagaaaaa ggaggagaga gatggcagaa gctgctggtg      60
gcggggcttc ttctgcagga tggaaatggc tctggacttg gcggtagctg atgccctcg     120 ctctgccgcc gcttggctct ggaccgcagc cgggtaatgg ctgctgcggc ggctgctgga    180
tggttgcagc gactgggcct gcttctcctc agcagccaga ggcctggcag cggcggcagc    240
ggaatgggga gaagacgaat aatcctccga acggctgcct ccgccggcgg cctccggagc    300
ccgggccacg ggggtgcgg cggcggcgca cgggaggttt aaaaccggcc cgggtccctg     360
gatgtgccag ccgccgccgc cgccgtgttg gaggcagtag aaggggagag accaactctc    420
cggcgttccc agccctggaa atggtgacag gcgactcaga ccccctccct ggagctgcag    480
ccgccgcggc cgccgccgcc gccgcttctc ccccccgctc caggagcggg aggtgccgcc    540
gccgccgccg cgcctcagcc ggctcccgcc cgagcccacg gcttccacct tcccttcag    600 gagaagccga ggaagaggct gcacggttag aaaagacgaa gaggaggcga gaaacgccgc    660
cgctgccgcc gccgcaggcc ggccggctcc ccgagggcgc tgccccgcg gctgctcaca    720 ggcgctgaga ggggctccgg gccgcggccg ccgccgtctc tcatctccct cgcctgagcc    780
cggcctcgcc tcacagcggc tcaactctca aacttccatc atggctgcag cttccgagag    840
gagagaactg agcgcagtcg cgtcccagcg ccgagcgcgt atcctgccgc agcgcataaa    900
gagtcccgcc acatcaccgc ccgccggcct gcccgccccc tccgccgccg cgccgggagc    960
ccgggcgcct cggaagaccg aggggaggcg ggaggcgagc gagaggcgga cgggaccgcg   1020
ccgggcgagg ggagg                                                    1035

<210> SEQ ID NO 2
<211> LENGTH: 953
<212> TYPE: DNA
<213> ORGANISM: Homo sapiens

<400> SEQUENCE: 2
gcagggcagg gcaggggcg gtaggagggg gcagagcggt agctctgggt gcgagcgcag       60
agtccccaag ccgcaggctc tactgagcat gcccagtgta gctgcctggg gcttgctcgg    120
gccggttccc agccgccagc ctgcagctgc acttgctgcg gcttttgcag caacgcgagg    180
cgaggataac gagctaagcc tcggcctctg cccagaaacc cagccggagg cagggtaggc    240
tgttgtgggg cggggtgga ggactgatga tgaaagctga gatgggtgcg ttgagcagtg     300
tcactgactc gagtctgagg ttacctgtgc acaggtgaaa aggaccaggt gaccacgctg    360
ctcagtgtag agggaaatgc agggacggtc cctgcaaggg gaatacccctc ccccctcgcc  420
```

```
tctacccta gatttccgcg gcgtggactg cattcgctct ttcctttgc accgctgtcg    480 gatcacaatc gttcgcagag atttgactgt aacagccttt gcctagagat tccccttcc    540 cccaaatctg tgtcctcatg gtgtcagtct tagcacaaag agcaacctgc tattgtgtcg    600
ccagcgtgta tcacctcatc cggctccctt gcagcgcccc acctctcgct tccccggtaa    660
ctcggctcgt ttgccctaaa aatgaaagct ctcagccgag cgtgctgaac gtgaacacat    720
agccgttgaa tttcaagggc ccaaagggca cctatctaaa tgaactgaaa gaggatccct    780
gtgagtggga cgcaccccgc aggcctctcc tgcgcccgct ccggtgcccc aagagagtc    840 gagcatcttt cccctcgggc tccaggtcgg ttcgcggcgt cggagtcaag ctcggttctc    900
agagaccacc tagccccgcc cccttggc cgccgtgaaa acccggcagg atg    953
```

```
<210> SEQ ID NO 3
<211> LENGTH: 290
<212> TYPE: DNA
<213> ORGANISM: Homo sapiens

<400> SEQUENCE: 3
gactgggcct gcttctcctc agcagccaga ggcctggcag cggcggcagc ggaatgggga    60
gaagacgaat aatcctccga acggctgcct ccgccggcgg cctccggagc ccgggccacg    120
gggggtgcgg cggcggcgca cgggaggttt aaaaccggcc cgggtccctg gatgtgccag    180
ccgccgccgc cgccgtgttg gaggcagtag aaggggagag accaactctc cggcgttccc    240
agccctggaa atggtgacag gcgactcaga cccctccct ggagctgcag    290
```

```
<210> SEQ ID NO 4
<211> LENGTH: 26
<212> TYPE: DNA
<213> ORGANISM: Artificial Sequence
<220> FEATURE:
<223> OTHER INFORMATION: PTEN ChIP forward promoter

<400> SEQUENCE: 4
aaagctagcc agactcgagt cagtga    26
```

```
<210> SEQ ID NO 5
<211> LENGTH: 24
<212> TYPE: DNA
<213> ORGANISM: Artificial Sequence
<220> FEATURE:
<223> OTHER INFORMATION: PTEN ChIP reverse primer

<400> SEQUENCE: 5
aaaagatctc gaggcggacg ggac    24
```

```
<210> SEQ ID NO 6
<211> LENGTH: 21
<212> TYPE: DNA
<213> ORGANISM: Artificial Sequence
<220> FEATURE:
<223> OTHER INFORMATION: KILLIN ChIP forward primer

<400> SEQUENCE: 6
gatggaagtt tgagagttga g    21
```

```
<210> SEQ ID NO 7
<211> LENGTH: 19
<212> TYPE: DNA
<213> ORGANISM: Artificial Sequence
<220> FEATURE:
```

<223> OTHER INFORMATION: KILLIN ChIP reverse primer

<400> SEQUENCE: 7
ccacggcttc caccttccc                                                19

<210> SEQ ID NO 8
<211> LENGTH: 28
<212> TYPE: DNA
<213> ORGANISM: Artificial Sequence
<220> FEATURE:
<223> OTHER INFORMATION: KILLIN RT forward primer

<400> SEQUENCE: 8
aaaagaattc cggggctggc gcttggggg                                     28

<210> SEQ ID NO 9
<211> LENGTH: 33
<212> TYPE: DNA
<213> ORGANISM: Artificial Sequence
<220> FEATURE:
<223> OTHER INFORMATION: KILLIN RT reverse primer

<400> SEQUENCE: 9
aaaagcggcc gcgtcctttg gcttgctctt agg                                33

<210> SEQ ID NO 10
<211> LENGTH: 21
<212> TYPE: DNA
<213> ORGANISM: Artificial Sequence
<220> FEATURE:
<223> OTHER INFORMATION: PTEN RT forward primer

<400> SEQUENCE: 10
cagaaagact tgaaggcgta t                                             21

<210> SEQ ID NO 11
<211> LENGTH: 17
<212> TYPE: DNA
<213> ORGANISM: Artificial Sequence
<220> FEATURE:
<223> OTHER INFORMATION: PTEN RT reverse primer

<400> SEQUENCE: 11
aacggctgag ggaactc                                                  17

<210> SEQ ID NO 12
<211> LENGTH: 22
<212> TYPE: DNA
<213> ORGANISM: Artificial Sequence
<220> FEATURE:
<223> OTHER INFORMATION: BS PCR forward primer

<400> SEQUENCE: 12
gttgtagttt tagggagggg gt                                            22

<210> SEQ ID NO 13
<211> LENGTH: 25
<212> TYPE: DNA
<213> ORGANISM: Artificial Sequence
<220> FEATURE:
<223> OTHER INFORMATION: BS PCR reverse primer

<400> SEQUENCE: 13
ctacttctcc tcaacaacca aaaac                                         25

```
<210> SEQ ID NO 14
<211> LENGTH: 15
<212> TYPE: DNA
<213> ORGANISM: Artificial Sequence
<220> FEATURE:
<223> OTHER INFORMATION: native sequence forward primer

<400> SEQUENCE: 14
aagggaaggt ggaag                                                        15

<210> SEQ ID NO 15
<211> LENGTH: 16
<212> TYPE: DNA
<213> ORGANISM: Artificial Sequence
<220> FEATURE:
<223> OTHER INFORMATION: native sequence reverse primer

<400> SEQUENCE: 15
ggcacatcca gggacc                                                       16

<210> SEQ ID NO 16
<211> LENGTH: 15
<212> TYPE: DNA
<213> ORGANISM: Artificial Sequence
<220> FEATURE:
<223> OTHER INFORMATION: forward primer for bisulfate-treated DNA

<400> SEQUENCE: 16
aagggaaggt ggaag                                                        15

<210> SEQ ID NO 17
<211> LENGTH: 16
<212> TYPE: DNA
<213> ORGANISM: Artificial Sequence
<220> FEATURE:
<223> OTHER INFORMATION: reverse primer for bisulfate-treated DNA

<400> SEQUENCE: 17
ggtatattta gggatt                                                       16
```

DIAGNOSIS OF COWDEN AND COWDEN-LIKE SYNDROME BY DETECTION OF DECREASED KILLIN EXPRESSION

CROSS-REFERENCE TO RELATED APPLICATIONS

This application claims priority to U.S. Provisional Patent Application No. 61/578,061, filed Dec. 20, 2011, which is incorporated herein by reference in its entirety.

GOVERNMENT FUNDING

The present invention was made, in part, with government support under National Cancer Institute Grant No. P01 CA 124570. The U.S. Government has certain rights in this invention.

BACKGROUND

Germline mutations of the phosphatase and tensin homolog (PTEN) gene (UCSC ID, uc001kfb.2; RefSeq, NM_000314), encoding deletions on chromosome 10, cause 25% of autosomal-dominant Cowden syndrome which minimally occur in 1 in 200,000 live births. These mutations result in a syndrome characterized by macrocephaly and typical mucocutaneous features (trichilemmomas, papillomatous papules) and hamartomas, with increased risk of various malignancies, approximately 28% lifetime risk for thyroid cancer, and as much as 50% lifetime risk for female breast cancer over the general population.

However, only 5% of this heterogeneous group referred to as having Cowden-like syndrome and who have some features of Cowden syndrome but do not meet diagnostic criteria, have germline PTEN mutations. In the absence of germline PTEN mutations, approximately 10% of individuals with Cowden syndrome or Cowden-like syndrome harbor germline succinate dehydrogenase variants SDHB and SDHD. Overall, germline PTEN mutations and deletions and SDHx variants account for 35% of Cowden syndrome and 6% to 11% of individuals with Cowden-like syndrome phenotypic features.

Cowden syndrome is a great clinical mimic and is difficult to recognize because every patient shows variable expression and penetrance. Importantly, many individuals in the general population share one or more features of Cowden syndrome but may not have Cowden syndrome and may not even harbor alterations in any predisposition genes. Many such patients present to primary care and other specialty clinicians who are called upon to recognize such individuals because individuals with specific gene mutations have increased risks of different spectra of neoplasias.

Somatic alterations of CpG island DNA hypermethylation and chromatin modification have been widely documented in human cancers. Jones et al., Cell, 128, 683-692 (2007). Regions in which CpG are exceptionally integrated are known as CpG islands. The CpG islands refer to sites which are 0.2-3 kb in length, and have a C+G content of more than 50% and a CpG ratio of more than 3.75%. There are about 45,000 CpG islands in the human genome, and they are mostly found in promoter regions regulating the expression of genes. In the case of genes whose mutations are attributed to the development of cancer in congenital cancer but do not occur in acquired cancer, the germline methylation of promoter CpG islands occurs instead of mutation. Typical examples include the promoter germline methylation of genes, such as acquired renal cancer VHL (von Hippel Lindau), breast cancer BRCA1, colorectal cancer MLH1, and stomach cancer E-CAD.

DNA methylation changes are not only detectable in tumors, but also in blood, as tumor-derived DNA is released into the bloodstream due to tumor necrosis and apoptosis. Cancer-specific DNA methylation alterations present in cancer tissues and blood of cancer patients can serve as diagnostic markers for risk assessment, progression, early detection, treatment prediction and monitoring. Laird, P. W., Nat Rev Cancer, 3, 253-266 (2003).

In the context of a difficult-to recognize syndrome, identification of additional cancer predisposition genes would facilitate molecular diagnosis, genotype-specific predictive testing of family members who are as yet clinically unaffected, genetic counseling, and medical management. Relevant to primary care, once a mutation or alteration is found, primary care physicians must have a basic understanding of gene-specific cancer risks as they do play and will increase their role as coordinators of gene-specific personalized management, surveillance, and other related factors of care.

SUMMARY

PTEN is a well-characterized tumor suppressor phosphatase involved in cellular regulation via G1 cell cycle arrest and apoptosis. Salmena et al., Cell 133(3): 403-414 (2008). Interestingly, a novel gene, KILLIN (UCSC, uc009xti.2; RefSeq, NM_001126049), which also resides in the 10q23.31 chromosomal region, is involved in cell cycle arrest and is regulated by TP53, similar to PTEN. PTEN and KILLIN share the same transcription start site but are transcribed in opposite directions. KILLIN has been shown to be necessary and sufficient for TP53-induced apoptosis. Cho et al., Proc Natl Acad Sci USA., 105(14): 5396-5401 (2008). This high-affinity DNA binding protein inhibits eukaryotic DNA synthesis in vitro and causes S phase arrest before apoptosis in vivo. Because of similar function to PTEN, KILLIN was investigated as a predisposition gene in patients with Cowden syndrome or Cowden-like syndrome.

Epigenetic alterations play an important role in cancer progression through hypermethylation and silencing of tumor suppressor genes, and somatic PTEN hypermethylation has been recognized as a means of PTEN downregulation in a subset of malignancies. When promoter CpG islands are methylated, the reason why the expression of the corresponding genes is blocked is not clearly established, but is presumed to be because a methyl CpG-binding protein or a methyl CpG-binding domain protein, and histone deacetylase, bind to methylated cytosine, thereby causing a change in the chromatin structure of chromosomes and a change in histone protein.

The inventors sought to address the hypothesis that germline methylation of the 10q23.31 bidirectional promoter CpG island (a region of at least 200 base pairs [bp] with a GC content of ≥50% and an observed and expected CpG ratio of >60%) silences PTEN, KILLIN, or both. This, consequently, would account for patients with Cowden syndrome or Cowden-like syndrome features but without germline PTEN mutations or deletions.

Accordingly, in one aspect, a method of diagnosing Cowden syndrome and Cowden-like Syndrome is provided. The method includes the steps of obtaining a biological sample from a subject; determining the level of expression of the KILLIN gene in the biological sample; and comparing the level of expression of the KILLIN gene in the biological sample to a control value for KILLIN gene expression;

wherein a lower level of expression of the KILLIN gene in the biological sample relative to the KILLIN expression control value provides a diagnosis that the subject has a substantially increased risk of having Cowden syndrome or Cowden-like syndrome.

In one embodiment, the level of KILLIN gene expression is measured by detecting the methylation of a KILLIN promoter region, wherein hypermethylation of the KILLIN promoter region indicates a lower level of KILLIN gene expression. In a further embodiment, the step of detecting methylation of the KILLIN promoter region includes the step of bringing the KILLIN promoter region into contact with sodium bisulfate under conditions suitable to modify unmethylated cytosine of the KILLIN promoter region into uracil. In a further embodiment, sodium bisulfate is used as part of a combined bisulfate restriction analysis.

In additional embodiments, the subject already has one or more symptoms of Cowden syndrome, such as breast cancer, thyroid cancer, or kidney cancer. In yet further embodiments, the method also includes the step of providing a therapeutic intervention for a subject identified as having a substantially increased risk of having Cowden syndrome or Cowden-like syndrome.

In another aspect, a kit for diagnosing Cowden Syndrome and Cowden-like Syndrome is provided. The kit may vary depending on the method used to detect DNA methylation. In one embodiment, the kit includes a carrier compartmentalized to include a plurality of containers and to receive a DNA sample including the KILLIN promoter region from a subject therein. The carrier includes a first container including sodium bisulfate, and the solvents and reagents necessary to selectively convert unmethylated cytosine of the DNA sample into uracil; a second container containing a PCR primer pair corresponding to the methylated base sequence of the KILLIN promoter region and the solvents and reagents necessary to obtain an amplified base sequence; and a third container containing a labeled probe complementary to the amplified base sequence. The kit also includes means for detecting the labeled probe to quantitatively analyze the amount of methylation of the KILLIN promoter region; and a KILLIN promoter region control.

In a further embodiment, the kit includes instructions for use of the kit to compare the amount of methylation of the KILLIN promoter region in the DNA sample to a KILLIN promoter region control. Hypermethylation of the KILLIN promoter region indicates a diagnosis of Cowden syndrome or Cowden-like Syndrome for the subject. The kit can use a PCR primer pair is selected from the group consisting of BS_PCR forward primer SEQ ID NO: 12 and BS_PCR reverse primer SEQ ID NO: 13. This PCR primer pair provides primers for DNA methylation analysis using the combined bisulfate restriction analysis method.

Another aspect provides a method for treating a subject having Cowden syndrome or Cowden-like syndrome by administering to the subject a therapeutically effective amount of a DNA methyltransferase inhibitor. In a further embodiment, the method also includes administering a histone deacetylase inhibitor to the subject. This method can be useful for a subject that has been found to lack germline PTEN mutation, since this indicates that it is more likely that the Cowden syndrome is a result of methylation of the KILLIN promoter region.

Additional features and advantages of the exemplary embodiments will be set forth in part in the description that follows, and in part will be obvious from the description, or may be learned by practice of the exemplary embodiments disclosed herein. The objects and advantages of the exemplary embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE FIGURES

The accompanying drawings, which are incorporated in and constitute a part of this specification, illustrate some embodiments disclosed herein, and together with the description, serve to explain principles of the exemplary embodiments disclosed herein.

FIG. 1 provides a sequence for the adjacent PTEN and KILLIN genes on chromosome 10. The sequence includes the PTEN gene (SEQ ID NO: 1), the KILLIN gene (SEQ ID NO: 2), and the KILLIN promoter region (SEQ ID NO: 3). The individual sequences are designated using square brackets. The PTEN and KILLIN genes are transcribed in opposite directions, as shown in FIG. 2. The KILLIN promoter region is embedded within the PTEN gene.

FIG. 3 provides experimental results and a pictoral representation of germline DNA methylation of PTEN and KILLIN in Cowden Syndrome and Cowden-like Syndrome. FIG. 3A, Example of combined bisulfite restriction analysis (COBRA) of polymerase chain reaction (PCR) products from a subset of patients with Cowden syndrome or Cowden-like syndrome (numbers refer to patient numbers). The 0% and 100% are from peripheral blood DNA, the 100% having been in vitro methylated with Sss I methylase. These serve as negative and positive controls for methylation pattern analysis of the patients. An increase in the intensity of smaller digested bands compared with the control samples indicates increased methylation in the tumor DNA. FIG. 3B, Results from bisulfite sequencing analysis of 8 of the patient samples. Each row of circles represents an individual cell clone. by indicates base pair.

DETAILED DESCRIPTION

Figure 2:
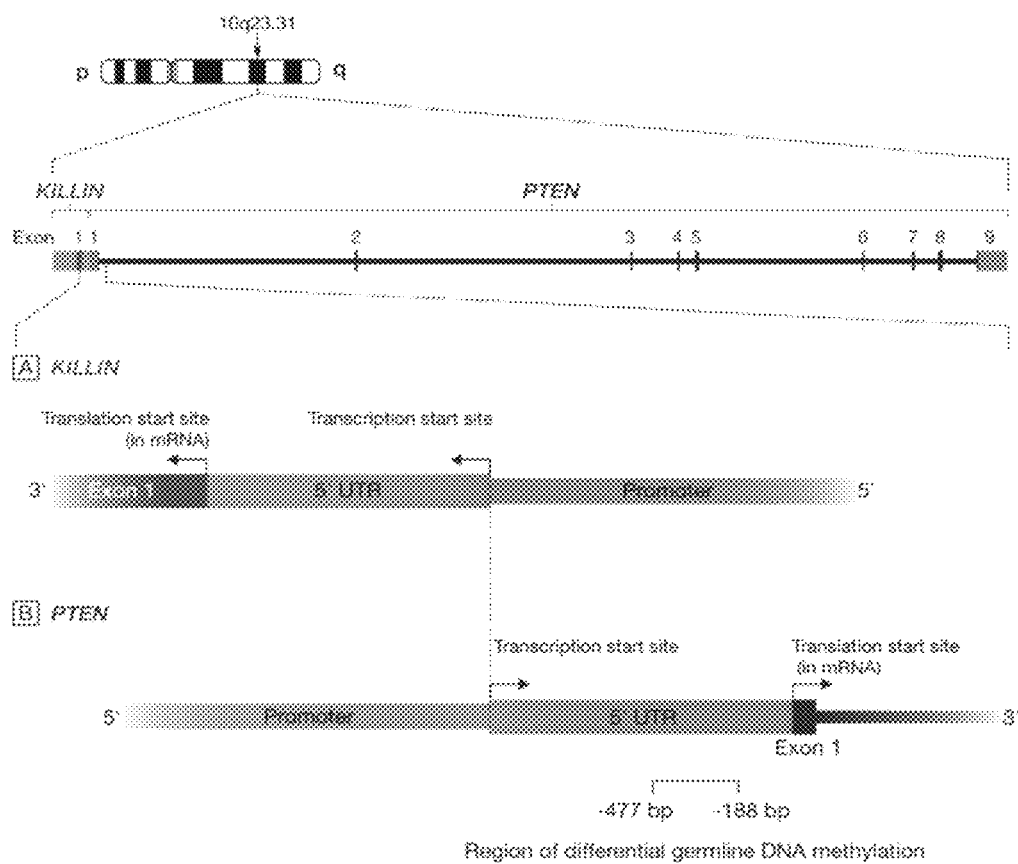
FIG. 2 provides a schematic of the Genomic Structure of the KILLIN and PTEN Genes on Chromosome 10. The region analyzed for DNA methylation is indicated, with the numbers showing the location of the bisulfite polymerase chain reaction product with respect to the translation start site (mRNA [messenger RNA]) of the PTEN gene. As depicted, the KILLIN promoter overlaps with the 5'UTR (untranslated region) and coding region of PTEN. bp indicates base pair.

The exemplary embodiments disclosed herein will now be described by reference to some more detailed exemplary embodiments, with occasional reference to the accompanying figures. These exemplary embodiments may, however, be embodied in different forms and should not be construed as limited to the embodiments set forth herein. Rather, these exemplary embodiments are provided so that this disclosure will be thorough and complete, and will fully convey the scope of the exemplary embodiments to those skilled in the art.

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

As used herein, the term "diagnosis" can encompass determining the presence and nature of disease or condition in a subject. "Diagnosis" can also encompass diagnosis in the context of rational therapy, in which the diagnosis guides therapy, including initial selection of therapy, modification of therapy (e.g., adjustment of dose and/or dosage regimen), and the like. Diagnosis does not imply certainty with regard to the nature of the disease or condition identified, but rather the substantial likelihood that the disease or condition is present. For example, a subject diagnosed as having Cowden syndrome may be 10× or 100× more likely to have Cowden syndrome relative to a subject that has not been diagnosed as having Cowden syndrome.

Diagnosis may be useful for early detection of a disease. As used herein, the term "early detection" of a disease (e.g., Cowden Syndrome and its associated cancers) refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

The terms "individual," "host," "subject," and "patient" are used interchangeably herein, refers to a species of mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos.

As used herein, the term "therapeutically effective amount" is meant an amount of a compound effective to yield the desired therapeutic response. For example, an amount effective to delay the growth of or to cause a cancer, either a sarcoma or lymphoma, or to shrink the cancer or prevent metastasis. The therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, "proliferative growth disorder, "neoplastic disease," "tumor; "cancer" are used interchangeably as used herein refers to a condition characterized by uncontrolled, abnormal growth of cells. Examples of cancer include but are not limited to, carcinoma, blastoma, and sarcoma. As used herein, the term "carcinoma" refers to a new growth that arises from epithelium, found in skin or, more commonly, the lining of body organs.

The term "in need of such treatment" as used herein refers to a judgment made by a care giver such as a physician, nurse, or nurse practitioner in the case of humans that a patient requires or would benefit from treatment. This judgment is made based on a variety of factors that are in the realm of a care giver's expertise, but that include the knowledge that the patient is ill, or will be ill, as the result of a condition that is treatable by the compounds of the invention.

A method of diagnosing Cowden Syndrome (CS) and Cowden-like Syndrome (CLS) is described herein. Cowden syndrome, which is also known as "Cowden's disease," and "Multiple hamartoma syndrome," is a rare autosomal dominant inherited disorder characterized by multiple tumor-like growths called hamartomas and an increased risk of certain forms of cancer. Cowden syndrome is associated with loss-of-function mutations in the tumor suppressor gene PTEN, leading to hyperactivity of the mTOR pathway. These mutations lead to characteristic features including macrocephaly, intestinal hamartomatous polyps, benign skin tumors (multiple trichilemmomas, papillomatous papules, and acral keratoses) and dysplastic gangliocytoma of the cerebellum (Lhermitte-Duclos disease). In addition, there is a predisposition to breast carcinoma, carcinoma of the thyroid, endometrial carcinoma, renal cell carcinoma, colorectal carcinoma and melanoma. Cowden-like syndrome is used to describe the disorder in which patients have many of the features of Cowden syndrome, but do not meet the formal diagnostic criteria.

In one embodiment, the method of diagnosing CS or CLS includes the steps of: (a) obtaining a biological sample from a subject; (b) determining the level of expression of the KILLIN (KLLN) gene in the biological sample; and (c) comparing the level of expression of the KILLIN gene in the biological sample to a control value for KILLIN gene expression. A lower level of expression of the KILLIN gene in the biological sample relative to the KILLIN expression control value provides a diagnosis that the subject has a substantially increased risk of having Cowden syndrome or Cowden-like syndrome.

Biological Samples

Biological samples include tissue samples (e.g., a portion of an organ), a cell sample (e.g., peripheral leukocytes) and biological fluids such as urine and blood-related samples (e.g., whole blood, serum, plasma, and other blood-derived samples), urine, cerebral spinal fluid, bronchoalveolar lavage, and the like. Methods of obtaining samples and/or extracting nucleic acid or protein from such samples are described herein and known to those skilled in the art.

A biological sample may be fresh or stored (e.g. blood or blood fraction stored in a blood bank). Samples can be stored for varying amounts of time, such as being stored for an hour, a day, a week, a month, or more than a month. The biological sample may be a biological fluid expressly obtained for the assays of this invention or a biological fluid obtained for another purpose which can be subsampled for the assays of this invention.

As used herein, the term "expression level of the KILLIN gene" refers to the amount of mRNA transcribed from the KILLIN gene that is present in a biological sample. The expression level can be detected with or without comparison to a level from a control sample or a level expected of a control sample. The expression level can be determined by measuring the amount of mRNA, or by measuring the amount of protein formed from the mRNA. The expression level of the KILLIN gene may be decreased by at least about 2 fold, at least about 5 fold, at least about 10 fold, at least about 20 fold, or at least about 50 fold.

A variety of methods may be used to determine the level of expression of the KILLIN gene. For example, the level of expression of the KILLIN gene can be obtained by determining the relative levels of mRNA being expressed using quantitative real-time polymerase chain reaction (qPCR). A key feature of qPCR is that the amplified DNA is detected as the reaction progresses in real time. This differs from standard PCR, where the product of the reaction is detected at its end. Two common methods for detection of products in real-time PCR are non-specific fluorescent dyes that intercalate with any double-stranded DNA, and sequence-specific DNA probes consisting of oligonucleotides that are labeled with a fluorescent reporter which permits detection only after hybridization of the probe with its complementary DNA target. See VanGuilder et al., Biotechniques 44 (5): 619-626 (2008).

Another method of determining the level of KILLIN gene expression is to purify the expressed Killin protein and directly determine its level of expression. Methods for purifying the Killin protein are described in U.S. Pat. No. 7,576,191, the disclosure of which is incorporated herein by reference. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified and/or quantified using chromatographic and electrophoretic techniques to achieve partial or complete purification (or purification to homogeneity). Analytical methods particularly suited to the preparation of a pure peptide are immunohistochemistry, ion-exchange chromatography, exclusion chromatography; polyacrylamide gel electrophoresis; isoelectric focusing. A particularly efficient method of purifying peptides is fast protein liquid chromatography or even HPLC.

Another embodiment of the method of diagnosing CS or CLS determines the level of KILLIN gene expression by detecting the level of methylation of the KILLIN promoter region. Hypermethylation of the KILLIN promoter region corresponds to a decreased level of KILLIN gene expression. As used herein, the term "hypermethylation" refers to the methylation state corresponding to an increased presence of 5-methyl-cytosine ("5-mCyt") at one or a plurality of CpG dinucleotides within a DNA sequence of a test DNA sample, relative to the amount of 5-mCyt found at corresponding CpG dinucleotides within a normal control DNA sample. In particular, hypermethylation refers to the methylation of a CpG island. As described herein, methylation of the KILLIN promoter results in decreased formation of the KILLIN promoter, resulting in a lower level of KILLIN expression.

The method of diagnosing CS or CLS includes the steps of: (a) obtaining a biological sample including DNA from a subject; (b) determining the level of methylation of the KILLIN promoter region in the biological sample; and (c) comparing the level of methylation of the KILLIN promoter region in the biological sample to a control value for KILLIN promoter expression. A higher level of methylation of the KILLIN promoter region in the biological sample relative to methylation of the KILLIN promoter region control value provides a diagnosis that the subject has a substantially increased risk of having Cowden syndrome or Cowden-like syndrome.

The method of diagnosing Cowden syndrome or Cowden-like syndrome includes the step of obtaining a biological sample including DNA from a subject. More specifically, the DNA is a DNA that includes the KILLIN promoter region (SEQ ID NO: 3). The biological sample including DNA can include any of the biological samples described herein. However, in some embodiments, it may be preferable to obtain the biological sample from tissue that has been characterized as being cancerous or precancerous. DNA (deoxyribonucleic acid), as is understood by those skilled in the art, is a molecule consisting of two long polymers of simple units called nucleotides with a backbone made of alternating sugars (deoxyribose) and phosphate groups that forms a double-stranded helix. The nucleotides include guanine, adenine, thymine, and cytosine, which are referenced using the letters G, A, T, and C. The term "nucleotide sequence," as used herein, refers to an oligonucleotide, nucleotide, or polynucleotide of single-stranded or double stranded DNA, or fragments thereof.

The KILLIN promoter is found within the KILLIN promoter region. The exact nucleotide sequence corresponding to the KILLIN promoter has not yet been identified, but it is known that a sequence within the KILLIN promoter region expresses the KILLIN promoter. The KILLIN promoter region may be part of a mixture of nucleic acids. The KILLIN promoter region may be a fraction of a larger molecule or can be present initially as a discrete molecule, so that the specific sequence constitutes the entire nucleic acid. It is not necessary that the sequence be present in a pure form; the nucleic acid may be a minor fraction of a complex mixture, such as contained in whole human DNA. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

DNA methylation is essential for normal development and is associated with a number of key processes including genomic imprinting, X-chromosome inactivation, suppression of repetitive elements, and carcinogenesis. Between 60% and 90% of all CpGs are methylated in mammals. Unmethylated CpGs are often grouped in clusters called CpG islands, which are present in the 5' regulatory regions of many genes. As used herein, the term "methylation" refers to the covalent attachment of a methyl group at the C5-position of the nucleotide base cytosine within the CpG dinucleotides of gene regulatory region. The term "methylation state" or "methylation status" or "methylation level" or "the degree of methylation" refers to the presence or absence of 5-mCyt at one or a plurality of CpG dinucleotides within a DNA sequence.

The present invention further encompasses the use of nucleotide sequences which are at least 85%, or at least 90%, or more preferably equal to or greater than 95% identical to the KILLIN promoter region (SEQ ID NO: 3). Sequence identity as used herein refers to the proportion of base matches between two nucleic acid sequences or the proportion amino acid matches between two amino acid sequences. When sequence homology is expressed as a percentage, e.g., 50%, the percentage denotes the proportion of matches over the length of sequence from one sequence that is compared to some other sequence.

Controls

Control values are based upon the level of KILLIN expression or methylation of the KILLIN promoter region in comparable samples obtained from a reference cohort. In certain embodiments, the reference cohort is the general population. For example, the reference cohort can be a select population of human subjects. In certain embodiments, the reference cohort is comprised of individuals who have not previously had any signs or symptoms indicating the presence of Cowden syndrome or Cowden-like syndrome.

The control value can take a variety of forms. The control value can be a single cut-off value, such as a median or mean. Control values for the level of KILLIN expression or the methylation of the KILLIN promoter region in biological samples obtained, such as for example, mean levels, median levels, or "cut-off" levels, are established by assaying a large sample of individuals in the general population or the select population and using a statistical model such as the predictive value method for selecting a positively criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference.

Method for Detection of Gene Methylation

The method of diagnosing Cowden Syndrome or Cowden-like Syndrome can include determining the level of methylation of the KILLIN promoter region in a biological sample. A wide variety of methods are available for determining gene methylation, such as methylation of the KILLIN promoter region. A number of these methods are described herein.

Detection of Differential Methylation-Methylation-Specific PCR

When genomic DNA is treated with bisulfite, cytosine in the 5'-CpG'-3 region remains intact, if it was methylated, but the cytosine changes to uracil, if it was unmethylated. Accordingly, the method of diagnosis can include the step of detecting methylation of the KILLIN promoter region includes the step of bringing the KILLIN promoter region into contact with sodium bisulfate under conditions suitable to modify unmethylated cytosine of the KILLIN promoter region into uracil. Based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Detection of Differential Methylation—Real-Time Methylation Specific PCR

Real-time methylation-specific PCR is a real-time measurement method modified from the methylation-specific PCR method and includes treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using SYBR green (an asymmetrical cyanine dye used as a nucleic acid stain). Real-time methylation-specific PCR allows selective quantitative analysis of methylated DNA. A standard curve is plotted using an in vitro methylated DNA sample, and a gene containing no 5'-CpG-3' sequence in the base sequence is also amplified as a negative control group for standardization to quantitatively analyze the degree of methylation.

Detection of Differential Methylation—Bisulfate Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid. This method is also referred to herein as combined bisulfate restriction analysis.

Examples of primers suitable for combined bisulfate restriction analysis are described in example 1. Other primers suitable for combined bisulfate restriction analysis of the KILLEN promoter region include a native sequence forward primer AAGGGAAGGTGGAAG (SEQ ID NO: 14); a native sequence reverse primer GGCACATCCAGGGACC (SEQ ID NO: 15); a forward primer for bisulfate-treated DNA AAGGGAAGGTGGAAG (SEQ ID NO: 16); and a reverse primer for bisulfate-treated DNA GGTATATTTAGGGATT (SEQ ID NO: 17).

Detection of Differential Methylation—Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

Detection of Differential Methylation—PCR Using Methylated DNA-Specific Binding Protein, Quantitative PCR, and DNA Chip Assay When a protein binding specifically to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

Detection of Differential Methylation—Methylation-Sensitive Restriction Enzyme

Detection of differential methylation can be accomplished by bringing a nucleic acid sample into contact with a methylation-sensitive restriction endonuclease that cleaves only unmethylated CpG sites. In a separate reaction, the sample is further brought into contact with an isoschizomer of the methylation-sensitive restriction enzyme that cleaves both methylated and unmethylated CpG-sites, thereby cleaving the methylated nucleic acid. Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI. The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers for use in the methods for detecting DNA methylation are designed to be "substantially" complementary to each strand of the locus to be amplified and include the appropriate G or C nucleotides. This means that the primers must be sufficiently complementary to hybridize with their respective strands under polymerization reaction conditions. The primers are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed. For example, in one embodiment of the invention, the PCR primers used selected from the group consisting of SEQ ID NO: 12 and SEQ ID NO: 13. In particular, these PCR primers are suitable for DNA methylation analysis using the combined bisulfate restriction analysis method.

The amplification reaction is the polymerase chain reaction (PCR) which is well known and commonly used in the art. However, alternative methods such as real-time PCR or linear amplification using isothermal enzyme may also be used. In addition, multiplex amplification reactions may also be used.

Symptoms of Cowden Syndrome

In some embodiments of the method of diagnosis, the subject has one or more symptoms of Cowden syndrome. For example, breast cancer, thyroid cancer, and kidney cancer are all symptoms of Cowden syndrome. Clinical features of Cowden syndrome are diverse, including breast, endometrial, thyroid, kidney and colorectal cancers, dermatologic features such as oral and skin papillomas, trichilemmomas, gastrointestinal features such as mixed polyposis including hamartomas, and neurologic features such as autism and Lhermitte Duclos disease. Diagnostic criteria have evolved over the years; the most recent is the Cleveland Clinic scoring system. Tan et al., American Journal of Human Genetics 88 (1): 42-56 (2011). For an individual patient, these features may be evaluated by the Cleveland Clinic web calculator to derive an individual probability of a relevant gene mutation.

The characteristic hamartomas of Cowden syndrome are small, noncancerous growths that are most commonly found on the skin and mucous membranes (such as the lining of the mouth and nose), but can also occur in the intestinal tract and other parts of the body. They are largely benign. However, people with Cowden syndrome have an increased risk of developing several types of cancer, including cancers of the breast, thyroid, and uterus.

Up to 75% have benign breast conditions such as ductal hyperplasia, intraductal papillomatosis, adenosis, lobular atrophy, fibroadenomas, and fibrocystic changes. Nonmedullary thyroid cancer develops in up to 10 percent of affected individuals. In addition, over one-half of those affected have follicular adenomas or multinodular goiter of the thyroid. Other malignancies that appear to be associated with Cowden and Cowden-like syndrome include endometrial and renal cancers. Other signs and symptoms of Cowden syndrome can include an enlarged head, a rare noncancerous brain tumor called Lhermitte-Duclos disease, and glycogenic acanthosis of the esophagus. The majority of affected individuals develop the characteristic skin lesions by age 20.

Kits

A kit for diagnosing Cowden syndrome and Cowden-like syndrome is also described. The kit includes a carrier compartmentalized to include a plurality of containers and to receive a DNA sample including the KILLIN promoter region from a subject therein. The kit includes a first container including sodium bisulfate, and the solvents and reagents necessary to selectively convert unmethylated cytosine of the DNA sample into uracil; a second container containing a PCR primer pair corresponding to the methylated base sequence of a KILLIN promoter region and the solvents and reagents necessary to obtain an amplified base sequence; and a third container containing a labeled probe complementary to the amplified base sequence. The kit also includes means for detecting the labeled probe to quantitatively analyze the amount of methylation of the KILLIN promoter region; and a KILLIN promoter region control.

The kit includes a carrier suited for containing one or more container means such as vials, tubes, and the like, each of the container means comprising one of the separate elements to be used in the method. In view of the description provided herein of the inventive method, those of skill in the art can readily determine the apportionment of the necessary reagents among the container means. The solvents and reagents necessary to convert unmethylated cytosine into uracil and to conduct PCR amplification of a methylated base sequence are known to those skilled in the art, and are referenced herein.

In other embodiments, kits designed to detect methylation of the KILLIN promoter region using DNA methylation detection methods other than bisulfate sequencing methods can be used. Examples of other DNA methylation detection include any of the DNA methylation detection methods described herein, such as pyro sequencing and cleavage of unmethylated CpG sizes using a methylation-sensitive restriction enzyme. For all of these kits, if a higher level of methylation of the KILLIN promoter region is found relative to that present in controls, or the KILLIN promoter region is found to be hypermethylated, this indicates that a subject evaluated using the kit can be diagnosed as having Cowden syndrome or Cowden-like syndrome.

An additional embodiment provides a kit for diagnosing CS or CLS using a methylation-sensitive restriction enzyme. In this embodiment, the kit includes carrier means compartmentalized to receive a sample therein; and one or more containers including a first container containing a reagent that sensitively cleaves unmethylated cytosine, a second container containing a PCR primer pair corresponding to the methylated base sequence of a KILLIN promoter region and the solvents and reagents necessary to obtain an amplified base sequence, and a third containing a means for detecting the presence of a cleaved or uncleaved nucleic acid. For example, one of the container means can include a container containing a methylation-sensitive restriction enzyme. One or more container means can also include a primer complementary to the KILLIN promoter region. In addition, one or more container means can also contain an isoschizomer of the methylation sensitive restriction enzyme.

In a further embodiment, a kit for diagnosing CS or CLS using pyrosequencing is provided. In this embodiment, the kit includes carrier means compartmentalized to receive a sample therein; and one or more containers including a first container containing sodium bisulfate, and the solvents and reagents necessary to selectively convert unmethylated cytosine of the DNA sample into uracil, and a second container containing a PCR primer pair corresponding to the methylated base sequence of a KILLIN promoter region and the solvents and reagents necessary to obtain an amplified base sequence. An additional container can be provided to conduct real-time base sequence analysis using a sequence primer, or this analysis can be conducted outside of the kit. In this embodiment, the degree of methylation is expressed as a methylation index by analyzing the amount of cytosine and thymine in the 5'-CpG-3' region of the KILLIN promoter region.

Primers contemplated for use in accordance with the present invention include any primers suitable for PCR amplification of the KILLIN promoter region. The primers can include a pair of PCR primer sequences for DNA methylation analysis that include a forward PCR primer and a reverse PCR primer, wherein the primers include from 20 to 25 nucleotides and are effective to amplify SEQ ID NO: 3 using the polymerase chain reaction. For example, the PCR primer pairs can be SEQ ID NO: 12 (the forward primer) and SEQ ID NO: 13 (the reverse primer), and any functional combination and fragments thereof.

Nucleic acid hybridization reactions are used in various steps described herein, including association of a labeled probe with the amplified base sequence. The conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An example of progressively higher stringency conditions is as follows: 2×SSC/0.1% SDS (sodium dodecyl sulfate) at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions).

The kit can include a labeled probe to analyze the amount of methylation. The probe of interest can be detectably labeled, for example, with a radioisotope, a fluorescent compound, a bioluminescent compound, a chemiluminescent compound, a metal chelator, or an enzyme. Appropriate labeling with such probes is widely known in the art and can be performed by any conventional method.

The kit can further include instructions for use of the kit to obtain a diagnosis for CS or CLS by compare the amount of methylation of the KILLIN promoter region in the DNA sample to a KILLIN promoter region control, wherein hypermethylation of the KILLIN promoter region indicates a diagnosis of Cowden syndrome or Cowden-like Syndrome for the subject. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Treatment of Cowden and Cowden-Like Syndrome in Subjects Having KILLIN Promoter Methylation and/or KILLIN Underexpression Further embodiments include providing a therapeutic intervention for a subject identified as having a substantially increased risk of having Cowden syndrome or Cowden-like syndrome. The therapeutic invention can be provided as a follow-up step to a diagnosis of a subject having Cowden syndrome or Cowden-like syndrome, either as a result of carrying out the method of diagnosis described herein or another suitable method for diagnosing Cowden syndrome or Cowden-like syndrome. A further embodiment provides a method for treating a subject lacks germline PTEN mutation and having Cowden syndrome or Cowden-like syndrome. As described herein, germline PTEN mutation is already known to be associated with a subset of Cowden syndrome and Cowden-like syndrome.

Therapeutic intervention for Cowden syndrome or Cowden-like syndrome can be provided to subject by administering to the subject a therapeutically effective amount of a DNA methyltransferase inhibitor. Alternately, or in addition, the method of therapeutic intervention can further including administering a histone deacetylase inhibitor to the subject.

DNA methyltransferase (DNMT) inhibitors, such as 5-aza-cytidine (5-aza-CR) and 5-aza-2'-deoxycytidine (5-aza-CdR) are widely studied because DNA hypomethylation induces the re-activation of tumor suppressor genes that are silenced by methylation-mediated mechanisms. The combination of histone deacetylase (HDAC) inhibitors or demethylating agents with other chemo-therapeutics can be used as a possible molecularly targeted therapeutic strategy. In particular, the combination of HDAC inhibitors with demethylating agents are effective since histones are connected to DNA by both physical and functional interactions. As such, the combination of HDAC and DNMT inhibition can be very effective (and synergistic) in inducing apoptosis, differentiation and/or cell growth arrest in human pancreatic lung, breast, thoracic, leukemia and colon cancer cell lines. Effective agents include HDAC inhibitors, such as, romidepsin, trichostatin A (TSA), sodium butyrate, depsipeptide (FR901228, FK228), valproic acid (VPA) and suberoylanilide hydroxamic acid (Vorinostat), and the demethylating agent, 5-aza-CdR used alone and in combination for the treatment of Cowden syndrome or Cowden-like syndrome, or cancer resulting therefrom, in subjects lacking germline PTEN mutation.

The following example is included for purposes of illustration and is not intended to limit the scope of the invention.

EXAMPLE

Example 1

Germline Epigentic Regulation of KILLIN in Cowden and Cowden-Like Syndrome

Germline loss-of-function phosphatase and tensin homolog gene (PTEN) mutations cause 25% of Cowden syndrome, a rare autosomal-dominant disorder (1 in 200,000 live births), characterized by high risks of breast, thyroid, and other cancers. A large heterogeneous group of individuals with Cowden-like syndrome, who have various combinations of Cowden syndrome features but who do not meet Cowden syndrome diagnostic criteria, have PTEN mutations less than 10% of the time, making molecular diagnosis, prediction, genetic counseling, and risk management challenging. Other mechanisms of loss of function such as hypermethylation, which should result in underexpression of PTEN or of KILLIN, a novel tumor suppressor transcribed in the opposite direction, may account for the remainder of Cowden syndrome and Cowden-like syndrome. Accordingly, the following experiments were carried out to determine whether germline methylation is found in Cowden syndrome or Cowden-like syndrome in individuals lacking germline PTEN mutations.

Methods

Patients

Between October 2005 and December 2009, 2000 patients with Cowden syndrome or Cowden-like syndrome were prospectively enrolled mainly regionally and also nationally by the Cleveland Clinic Genomic Medicine Institute in accordance with research protocol (IRB8458-PTEN) and approved by the respective institutional review boards for human subjects protection. All research participants provided written informed consent. To be enrolled in the IRB8458-PTEN, individuals are eligible if they meet the full Cowden syndrome diagnostic criteria established by the International Cowden Consortium (i.e., major criteria include breast cancer, thyroid cancer, macrocephaly, endometrial carcinoma, Lhermitte-Duclos disease) according to version 2000 (Table 1). Pilarski et al., J Med Genet., 41(5): 323-326 (2004). Patients meeting the relaxed criteria are referred to as individuals with Cowden-like syndrome phenotypes (or CSL).

Table 1: International Cowden Consortium Operational Diagnostic Criteria for CowdenSyndrome (2000)

Pathognomonic Criteria
Mucocutaneous lesions:
    Mucosal lesions
    Trichilemmomas (facial)
    Papillomatous lesions
    Acral keratoses
    Major Criteria
Breast cancer
Thyroid cancer, especially follicular thyroid cancer
Macrocephaly (occipital frontal circumference 97th percentile)
Endometrial carcinoma
Lhermitte-Duclos disease, defined as presence of a cerebellar dysplastic gangliocytoma
Minor criteria
Other thyroid lesions (e.g., goiter)
Mental retardation (IQ 75)
Hamartomatous intestinal polyps
Fibrocystic disease of the breast
Lipomas
Fibromas
Genito-urinary tumors (for example, uterine fibroids, renal cell carcinoma) or genito-urinary malformation Operational Diagnosis if an Individual Meets any One of the Following Criteria:
  Pathognomonic mucocutaneous lesions alone if there are:
    Six or more facial papules, of which three or more must be trichilemmoma, or
    Cutaneous facial papules and oral mucosal papillomatosis, or
    Oral mucosal papillomatosis and acral keratoses, or
    Six or more palmo plantar keratoses
  Two or more major criteria (one must be macrocephaly or Lhermitte-Duclos disease)
  One major and at least three minor criteria
  At least four minor criteria
Relatives of Individuals with Cowden Syndrome are Considered to have a Diagnosis of CS if they Meet any of the Following Criteria:
  The pathognomonic criteria
  Any one major criterion with or without minor criteria
  Two minor criteria Of the 2000 prospectively enrolled participants meeting the criteria for protocol IRB8458-PTEN, fewer than 400 lacked germline PTEN pathogenic mutations, large deletions, variants of unknown significance, and polymorphisms by sequencing analysis of all nine exons and the promoter. Of these 400, we selected a nested series of the most recent 123 participants who also were found not to have SDHB/D variation, regardless of family history status, comprising 48 with Cowden syndrome, 75 with Cowden-like syndrome, and 50 unaffected individuals (population controls resident in the region), for the purposes of this study. Sample sizes were selected to ensure power (P>0.90) to detect a 5% prevalence of the methylation, as well as to detect a 3-fold difference between case and control participants.

All specimens from study and control participants were prepared and analyzed within the Genomic Medicine Institute. The majority of the participants were isolated cases, with the exception of three individuals, each of whom had at least one family member who also agreed to be part of our study. All analyses were performed from August 2008 through June 2010.

Analysis of Germline Hypermethylation

The combined bisulfite restriction analysis (COBRA; Bennett et al., Cancer Res.; 67(10): 4657-4664 (2007)) and the bisulfite sequencing were performed as previously described. Tada et al., J. Natl Cancer Inst.; 98(6): 396-406 (2006). The bisulfite polymerase chain reaction (BS-PCR) primer sequences are shown in Table 2. To provide a comprehensive analysis of the methylation status across the CpG islands upstream of PTEN, we screened four different regions (+400 bp to +700 bp; −188 bp to −477 bp; −425 bp to −640 bp; −806 bp to −1043 bp, all with respect to the PTEN translation start site).

TABLE 2

Primer Sequences

| Primer | Sequence (5' to 3') | Tm |
| --- | --- | --- |
| PTEN_ChIP_F | AAAGCTAGCCAGACTCGAGTCAGTGA (SEQ ID NO: 4) | 55 |
| PTEN_ChIP_R | AAAAGATCTCGAGGCGGACGGGAC (SEQ ID NO: 5) | 55 |
| KILLIN_ChIP_F | GATGGAAGTTTGAGAGTTGAG (SEQ ID NO: 6) | 62 |
| KILLIN_ChIP_R | CCACGGCTTCCACCTTCCC (SEQ ID NO: 7) | 62 |
| KILLIN_RT_F | AAAAGAATTCCGGGGCTGGCGCTTGGGG (SEQ ID NO: 8) | 60 |
| KILLIN_RT_R | AAAAGCGGCCGCGTCCTTTGGCTTGCTCTTAGG (SEQ ID NO: 9) | 60 |
| PTEN_RT_F | CAGAAAGACTTGAAGGCGTAT (SEQ ID NO: 10) | 60 |
| PTEN_RT_R | AACGGCTGAGGGAACTC (SEQ ID NO: 11) | 60 |
| BS_PCR_F | GTTGTAGTTTTAGGGAGGGGT (SEQ ID NO: 12) | 60 |
| BS_PCR_R | CTACTTCTCCTCAACAACCAAAAAC (SEQ ID NO: 13) | 60 |

Cell Lines, Antibodies, and Plasmids

The patient and control lymphoblastoid cell lines used in this study were generated from peripheral blood samples by the Genomic Medicine Biorepository of the Cleveland Clinic Genomic Medicine Institute.

Promoter luciferase assay was performed in order to validate transcriptional repression by DNA promoter methylation and differential inhibition of TP53 binding. Breast cancer cell line MDA-MB-453 (American Type Culture Collection) was used for the luciferase assay. Lymphoblastoid cell lines and MDA-MB-453 (M. D. Anderson metastatic breast cancer) were maintained in RPMI (Rosewall Park Memorial Institute) medium with 10% fetal bovine serum and 2% antibiotics. The antibody used in the chromatin immunoprecipitation analysis (ChIP) experiment was mouse monoclonal TP53 (Santa Cruz; sc-126). The in vitro methylated constructs used for the luciferase assay were generated by first digesting 90 μg of the original PTEN and KILLIN promoter constructs (containing 1 to 1344 bp upstream of the PTEN translational start site cloned in either direction) with Bgl II (New England Biolabs, Ipswich, Mass.) and Bbv CI (New England Biolabs). The linearized, digested inserts and vectors were gel extracted. The insert DNA, which contain the sequence that is methylated in vivo in patients with Cowden syndrome or Cowden-like syndrome, was then methylated with CpG Sss I methylase (New England Biolabs) for 4 hours. Following in vitro methylation, the insert was religated with its corresponding vector using a 3:1 insert to vector ratio with 2 µg total DNA. For comparison, the unmethylated counterpart was digested and religated in parallel.

Chromatin Immunoprecipitation Analysis

ChIP analysis was performed in order to validate that TP53 binding is differentially affected by DNA methylation and performed as previously described, (Bennett et al., Cancer Res.; 67(10): 4657-4664 (2007)) according to the Upstate Cell Signaling Solutions protocol. ChIP analysis utilized two controls and four patients that were selected based on methylation status, representation of Cowden syndrome and Cowden-like syndrome, and similar levels of KILLIN mRNA down-regulation. Sequences of the primers used for the quantitative ChIP PCRs can be found in Table 2.

Luciferase Assays

Luciferase assays were performed as previously described using MDA-MB-453 cells. Yu et al. Genomics.; 84(4): 647-660 (2004).

Reverse Transcription Polymerase Chain Reaction

The quantitative reverse transcription PCRs were performed as previously described. Bennett et al., Cancer Res.; 67(10): 4657-4664 (2007). The study population included four controls and eight patients that were selected based on confirmed methylation status by bisulfite sequencing analysis and representation of the Cowden syndrome and Cowden-like syndrome condition.

Demethylation and Histone Deacetylation Inhibition Treatment

The study population included eight patients that were selected based on confirmed methylation status by bisulfite sequencing analysis and representation of Cowden syndrome and Cowden-like syndrome condition. Demethylation treatment was performed with a cytosine analog, 5-aza-2'deoxycytidine (decitabine; Sigma), for 96 hours at 0.5 µM concentration with approximately 40% confluent suspension lymphoblastoid cells. Inhibition of histone deacetylation was performed with 200 nM concentration of Trichostatin A (TSA; Sigma) with approximately 40% confluent suspension lymphoblastoid cells for 48 hours, with or without 0.5 µM decitabine. The drug was changed daily, and the cells were collected for RNA isolation.

Statistical Analysis

The statistical significance of the results from reverse transcription PCR and luciferase assays was calculated by unpaired t test, with P<0.05 being considered statistically significant, using Microsoft Excel version 12.2.5. The prevalence of component malignancies between KILLIN promoter methylation-positive patients and germline pathogenic PTEN mutation-positive patients was compared using the Fisher 2-tailed exact test with P<0.05 considered to be significant.

Results

Germline Methylation in PTEN Mutation-Negative Cowden Syndrome and Cowden-Like Syndrome We analyzed germline genomic DNA from patients with Cowden syndrome or Cowden-like syndrome and from population controls for methylation upstream of PTEN using COBRA. Differential germline methylation was detected between 188 and 477 bp upstream of the translation start site for PTEN (FIG. 1). All controls showed no methylation (FIG. 2A). Among the 123 Cowden syndrome/Cowden-like syndrome samples analyzed, 45 (37%) were hypermethylated compared with all 50 controls (FIG. 2A). Twenty of the 48 (42%) classic Cowden syndrome patients without germline PTEN mutations showed germline hypermethylation. Of the 75 PTEN mutation-negative Cowden-like syndrome patients, 25 (33%) were found to have germline hypermethylation. Bisulfite sequencing analysis confirmed these differences in a set of Cowden syndrome and Cowden-like syndrome samples (FIG. 2B).

We then investigated whether methylation segregates with disease in family members of a proband with germline methylation. Of the 45 participants with methylation, only one proband had more than one affected family member and more than one unaffected family member who agreed to enroll in this study. We found germline methylation in four of six of the family members, and three of these four had documented Cowden syndrome/Cowden-like syndrome features (with one unknown phenotype). The two remaining unaffected family members did not have germline methylation (30%; 95% confidence interval, 7%-45%; P=0.008).

Germline Methylation and Effect on PTEN and KILLIN Expression

Promoter methylation should result in decreased expression of the relevant gene. In order to validate the pathogenic relevance of this methylation, the expression of PTEN was analyzed in four control and eight patient cell lines as proof of principle. PTEN expression in the methylated patient samples was surprisingly not decreased, and instead, increased PTEN expression was noted (FIG. 3). The PTEN 5'UTR and coding region analyzed for methylation overlaps with the putative promoter for KILLIN, a newly characterized tumor suppressor gene (FIG. 1). Cho Y J, Liang P. Proc Natl Acad Sci USA.; 105(14): 5396-5401 (2008). Therefore, in order to address our hypothesis that germline methylation upstream of PTEN may, instead, be silencing KILLIN, we then analyzed KILLIN expression in the patient samples that showed germline methylation. In the methylated patient samples tested, significant underexpression of KILLIN was observed compared with the control samples (250-fold; 95% confidence interval, 45-14 286; P=0.007) (FIG. 3).

Figure 4:
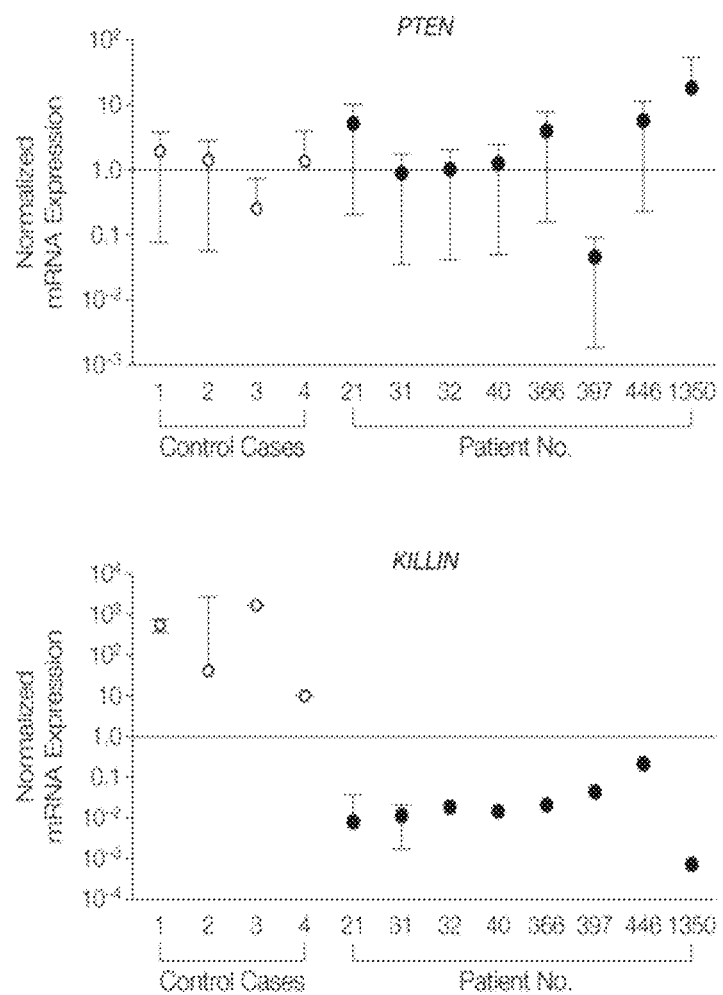
FIG. 4 provides graphs showing the results of quantitative mRNA analysis of PTEN and KILLIN Expression with germline methylation in controls and patients With Cowden Syndrome or Cowden-like Syndrome. Quantitative reverse transcription polymerase chain reaction analysis of four controls and eight patient samples. All samples were first normalized to their own internal control (GAPDH). The average of the controls, set to 1, was used for normalization for all samples. The top panel displays the expression for PTEN, which reveals significantly increased expression (at the P<0.05 threshold) in 3 patient samples (patients 21, 446, and 1350) compared with the controls, while only 1 sample showed significantly decreased expression (patient 397). The bottom panel reveals significantly decreased KILLIN expression in all patient samples analyzed. Error bars indicate 95% confidence intervals; mRNA, messenger RNA.

If, in fact, germline methylation down-regulates KILLIN expression, then demethylation should restore KILLIN expression. DNA methylation and histone deacetylation of the promoter often work together to achieve gene silencing, and histone acetylation has previously been shown to be transcriptionally relevant in the vicinity of the PTEN-KILLIN bidirectional promoter. Therefore, we investigated whether reversal of these epigenetic modifications, via demethylation and/or inhibition of histone deacetylation, would restore only KILLIN expression. KILLIN-methylated patient lymphoblastoid cell lines were treated with the demethylating drug decitabine and/or the histone deacetylase inhibitor TSA. Demethylation and/or inhibition of histone deacetylation led to a significant decrease in PTEN expression for seven of the eight (88%) patient cell lines (FIG. 4). In contrast to PTEN, KILLIN expression was restored in 88% (7 of the 8) analyzed patient cell lines following exposure to decitabine and/or TSA (increased 4.88-fold; 95% confidence interval, 1.4-18.1) (FIG. 4).

Germline Methylation Affects TP53 Binding to the KILLIN Promoter

Figure 5:
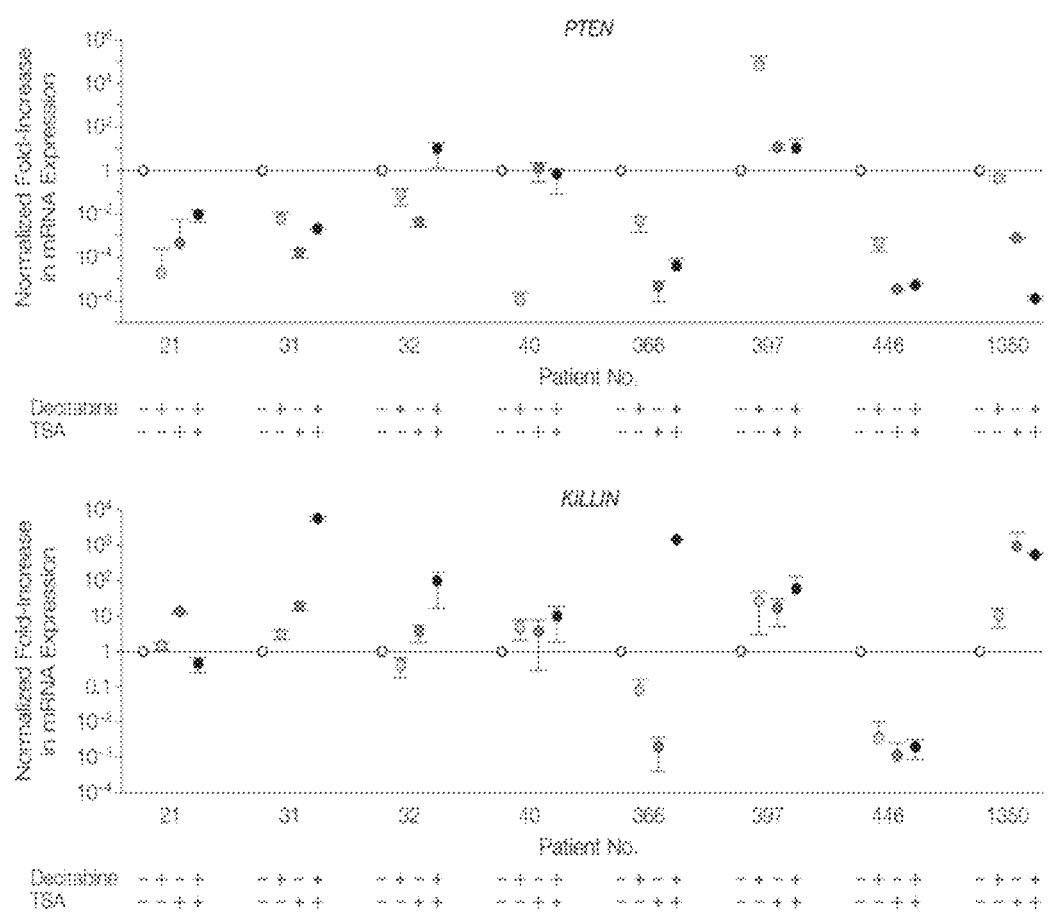
FIG. 5 provides graphs showing the results of quantitative mRNA analysis of PTEN and KILLIN expression with germline methylation, with and without demethylation and histone deacetlyase inhibition treatment. Quantitative reverse transcription polymerase chain reaction analysis was performed on the complementary DNA from cells with (+) and without (−) drug exposure (see "Methods" section) to detect changes in expression from the demethylation and histone deacetylase inhibition treatment. All values were first normalized to their internal control (GAPDH). The fold increase or decrease in expression in the drug-treated samples is derived by normalizing to its untreated counterpart, which was set as 1. PTEN expression is shown on the top panel and reveals a significant decrease in PTEN expression following demethylation in all but 1 cell line. Patient 397 that showed an increase in PTEN expression following demethylation treatment alone was not significant (P=0.42). The bottom panel shows KILLIN expression following demethylation and/or inhibition of histone deacetylation, which shows a significant increase in expression in 7 of 8 cell lines (patient 446 was the exception). mRNA indicates messenger RNA. Error bars indicate 95% confidence intervals.

Because the methylation of the shared bidirectional promoter had a differential impact on transcription for these two genes, we sought to mechanistically explain what might account for the differential epigenetic control. Both genes are transcriptionally regulated by TP53, and there appears to be two distinct TP53 binding sites—one for KILLIN and the other for PTEN. The TP53 binding site for transcriptional activation of PTEN lies outside of our germline methylated region (Stambolic et al., Mol Cell. 2001; 8(2): 317-325 (2001)), whereas the putative TP53 binding site for KILLIN lies within the methylated region identified in this study (FIG. 5). Therefore, if we are correct that the methylation down-regulates only KILLIN expression, then the methylation should exclusively inhibit TP53 binding and activation for KILLIN alone, without affecting PTEN transcription (FIG. 5).

Figure 6:
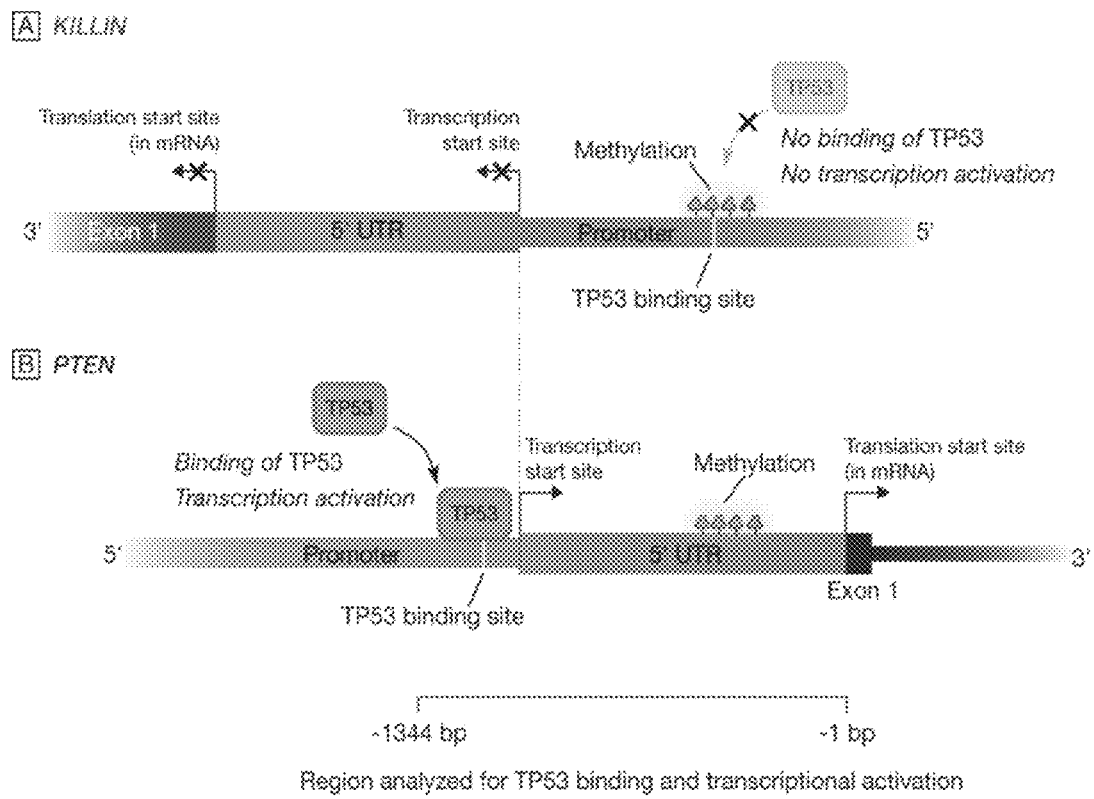
FIG. 6 provides a schematic showing the effect of methylation on transcription of KILLIN and PTEN. The model depicts where the observed methylation resides with respect to both KILLIN and PTEN and shows the regions where TP53 binds for PTEN and is blocked from binding for KILLIN transcriptional activation. mRNA indicates messenger RNA; UTR, untranslated region; bp, base pair.

One powerful way to interrogate this is by ChIP analysis: if there is no methylation "blocking" the relevant TP53 binding sites, then ChIP should reveal the TP53-associated regions of DNA by "pulling down" the sites bound by TP53 protein via the use of a TP53 antibody. Accordingly, we utilized four lines from patients who exhibited germline methylation of the KILLIN promoter and found that in three patients, TP53 bound more strongly to its PTEN binding site and relatively poorly to its KILLIN binding site, which was blocked by methylation (FIG. 6). As controls, ChIP analysis revealed no difference of TP53 binding to both the PTEN and KILLIN TP53 binding sites in the unmethylated control cell lines tested (FIG. 6).

Figure 7:
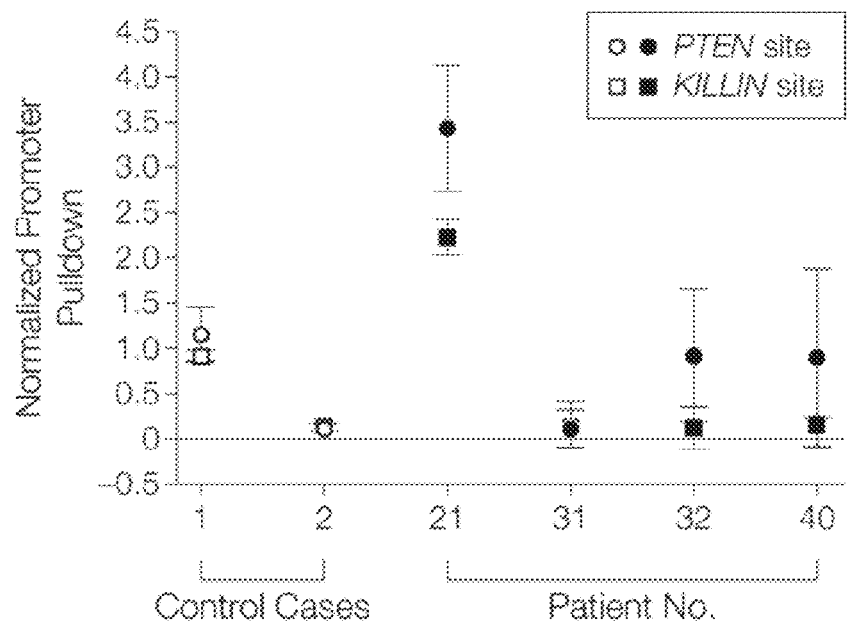
FIG. 7 provides a graph showing the results of chromatin immunoprecipitation analysis. Chromatin immunoprecipitation analysis of TP53 pulldown of either KILLIN's or PTEN's TP53 binding element in controls and Cowden syndrome patients. All samples are normalized to their negative control, IgG. Varied enrichment of the KILLIN and PTEN TP53 binding sites was observed in the control samples, whereas a significantly greater amount of region 1 (PTEN's TP53 binding site) was pulled down in 3 of 4 patient cell lines (patient 31 was the exception). Error bars indicate 95% confidence intervals.
Figure 8:
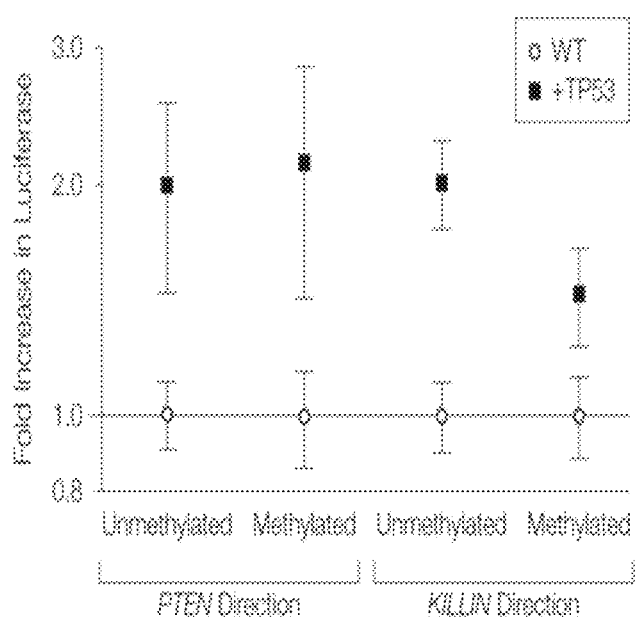
FIG. 8 provides a graph showing a comparison of transcriptional activation following methylation of the same promoter sequence in KILLIN and PTEN. In vitro methylation with Sss I methylase was performed for both the PTEN and KILLIN luciferase promoter constructs. The constructs contained the same promoter sequence (either in orientation for KILLIN or in the opposite orientation for PTEN), which includes 1 to 1344 base pair of sequence upstream of the translation start site of PTEN. Luciferase promoter analysis of PTEN and KILLIN promoter activity was done using the MDA-MB-453 breast cancer cells in the absence (wild-type [WT]) or presence (+TP53) of TP53 transfection. All values were first normalized to their internal control, *Renilla luciferase*. The fold increase in the samples with TP53 overexpression was attained by normalization to those without TP53 transfection, which was set as 1. The PTEN constructs showed significant activation by TP53 regardless of methylation status (P=0.01). However, the KILLIN-methylated construct showed significantly less activation by TP53 compared with the unmethylated KILLIN luciferase construct (P=0.008). The WT analysis was not significant (P=0.78). Error bars indicate 95% confidence intervals.

To further address whether the differential TP53 binding of these two regions is due to methylation seen in the patient samples, we artificially and purposefully methylated the same CpG region in a PTEN or KILLIN promoter construct. By overexpressing TP53 in these cells, we observed a significant increase in PTEN promoter activity, without significant differences in the level of activation between the unmethylated and methylated PTEN constructs (FIG. 7). Although both the unmethylated and methylated KILLIN constructs also provided an increase in transcriptional activation with TP53 overexpression, the methylated KILLIN construct showed significantly less transcriptional activation (30%; 95% confidence interval, 7%-45%; P=0.008) by TP53 compared with the unmethylated KILLIN construct or the PTEN constructs (FIG. 7).

Prevalent Cancers in Pathogenic PTEN Mutation Positive vs KILLIN Methylation-Positive Patients We then turned our attention to the prevalence of component malignancies in those with germline KILLIN promoter methylation and those with proven pathogenic germline PTEN mutations. We found a significant association between the KILLIN methylation status and prevalence of female breast cancer. In our 42 women with methylation, 35 had invasive breast cancers compared with 24 of 64 women (from the same IRB8458-PTEN series) with germline PTEN pathogenic mutations (P<0.0001). Renal cell carcinoma was overrepresented in the methylation-positive participants over PTEN mutation-positive individuals (4/45 vs 6/155; P=0.004). However, no differences in prevalent thyroid cancers or endometrial cancers were found between the two groups (P=0.2 and 0.4, respectively). Among the twelve epithelial thyroid carcinomas in individuals with KILLIN methylation-positive Cowden syndrome/Cowden-like syndrome, seven were classic papillary thyroid carcinomas compared with the five classic papillary thyroid carcinomas to ten follicular thyroid carcinoma/follicular variant of papillary thyroid carcinoma ratio seen in PTEN mutation-positive individuals.

COMMENTS AND CONCLUSIONS

Individuals with heritable syndromes, such as hereditary nonpolyposis colorectal cancer, who are negative for mutations in the known predisposition genes have rarely been shown to have heritable hypermethylation (also known as epimutation) of the respective promoters of these genes. Hitchins et al., N Engl J. Med.; 356(7): 697-705 (2007). This guided our initial hypothesis that a subset of patients with Cowden syndrome/Cowden-like syndrome without PTEN mutations would possibly have PTEN promoter hypermethylation. Instead, our alternative hypothesis was proven correct, resulting in our uncovering a novel Cowden syndrome/Cowden-like syndrome predisposition gene, KILLIN, and a new mechanism of epimutation that contributes to the pathogenesis of Cowden syndrome/Cowden-like syndrome features in individuals without germline PTEN mutations. The bidirectional promoter is affected by the distinct mechanism of exclusive disruption of TP53 binding and activation of KILLIN, while TP53 regulation of PTEN (the latter is outside of the methylated region) remains unaffected.

The germline KILLIN promoter epigenetic modification mechanism described here accounts for one-third of germline PTEN mutation-negative Cowden syndrome and of those whose phenotypic features resemble Cowden syndrome, prominently those with breast and thyroid disease. In our current series, more than 40% of PTEN mutation-negative classic Cowden syndrome and 33% of mutation-negative Cowden-like syndrome patients have germline epigenetic inactivation of the KILLIN promoter. If these data can be and must be replicated independently, then a hypothetical schema for prioritizing gene testing could be as follows: (1) individuals with classic Cowden syndrome should be offered PTEN testing first; (2) those found not to have germline PTEN mutations should then be offered KILLIN epigenetic analysis, in the setting of genetic counseling; and (3) individuals with classic Cowden syndrome without germline PTEN mutation (80% are mutation-positive) and without KILLIN epigenetic inactivation (half of the 20% should have KILLIN epigenetic inactivation) should then be offered SDHB/D testing (10% of the 20% should have SDHB/D mutation). Altogether, therefore, PTEN, KILLIN, and SDHB/D should then account for 92% of all classic Cowden syndrome. Patients with Cowden-like syndrome features, especially where breast cancer and/or renal carcinomas are present in the individual or family (or both) should be offered KILLIN methylation analysis first because it accounts for 30% of such patients compared with PTEN mutations, which only account for 5% to 10% of such individuals.

By discovering another cancer predisposition gene, we have added to the sensitivity of molecular diagnosis and predictive testing becomes possible. Importantly, genetic counseling and gene-informed risk assessment and management become evidence based. In contrast to germline PTEN mutations, germline methylation of the KILLIN promoter confers a significantly higher prevalence of female invasive breast cancer and renal cell carcinomas. The current national practice guidelines for individuals with PTEN germline mutations includes heightened surveillance of the female breasts and thyroid, but do not have awareness of renal cancer risk. If our observations of 2- to 3-fold increased risks of renal and/or breast cancer with KILLIN germline methylation over those of PTEN mutation holds, then extra vigilance for the organs at risk, breast and kidneys, is warranted. The KILLIN-associated breast cancer risks would parallel those conferred by germline BRCA1/2 mutations.

Among patients with Cowden syndrome or Cowden-like syndrome, presence of germline KILLIN gene promoter hypermethylation was common and was associated with increased risk of breast and renal cancer compared with PTEN mutation-positive patients.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A method of diagnosing Cowden syndrome and Cowden-like Syndrome in a subject, the method comprising the steps of:
   (a) obtaining a biological sample from a subject;
   (b) determining the level of expression of the KILLIN gene in the biological sample, wherein the level of KILLIN gene expression is measured by detecting the methylation of a KILLIN promoter region by combined bisulfate restriction analysis,
   wherein the PCR primers used in the combined bisulfate restriction analysis comprise SEQ ID NO: 12 and SEQ ID NO: 13,
   wherein hypermethylation of the KILLIN promoter region indicates a lower level of KILLIN gene expression;
   (c) comparing the level of expression of the KILLIN gene in the biological sample to a control value for KILLIN gene expression; and
   (d) providing a diagnosis that the subject has an increased risk of having Cowden syndrome or Cowden-like syndrome if there is a lower level of expression of the KILLIN gene in the biological sample relative to the KILLIN expression control value.

2. The method of claim 1, wherein the KILLIN promoter region comprises a nucleotide sequence having at least 85% sequence identify to SEQ ID NO: 1.

3. The method of claim 1, wherein the KILLIN promoter region comprises a nucleotide sequence having at least 95% sequence identify to SEQ ID NO: 1.

4. The method of claim 1, wherein the biological sample is blood.

5. The method of claim 1, wherein the subject is human.

6. The method of claim 1, wherein the subject has one or more symptoms of Cowden syndrome.

7. The method of claim 6, wherein the one or more symptoms of Cowden syndrome are selected from breast cancer, thyroid cancer, and kidney cancer.

8. The method of claim 1, further comprising the step of providing a therapeutic intervention for a subject identified as having a increased risk of having Cowden syndrome or Cowden-like syndrome.

9. The method of claim 8, wherein therapeutic intervention comprises administration of a DNA methyltransferase inhibitor or a histone deacetylase inhibitor to the subject.

* * * * *